(12) United States Patent
Furno et al.

(10) Patent No.: US 8,829,107 B2
(45) Date of Patent: Sep. 9, 2014

(54) BIODEGRADABLE SUPERABSORBENT POLYMER COMPOSITION WITH GOOD ABSORPTION AND RETENTION PROPERTIES

(75) Inventors: Franck Furno, Düsseldorf (DE); Harald Schmidt, Mülheim an der Ruhr (DE); Nicolaas De Bruin, Krefeld (DE)

(73) Assignee: Evonik Degussa GmbH, Essen (DE)

( * ) Notice: Subject to any disclaimer, the term of this patent is extended or adjusted under 35 U.S.C. 154(b) by 613 days.

(21) Appl. No.: 12/280,654

(22) PCT Filed: Feb. 28, 2007

(86) PCT No.: PCT/EP2007/001712
§ 371 (c)(1),
(2), (4) Date: Dec. 9, 2008

(87) PCT Pub. No.: WO2007/098932
PCT Pub. Date: Sep. 7, 2007

(65) Prior Publication Data
US 2010/0057027 A1    Mar. 4, 2010

(30) Foreign Application Priority Data
Feb. 28, 2006   (DE) .......................... 10 2006 009 579

(51) Int. Cl.
| | | |
|---|---|---|
| C08L 31/00 | (2006.01) | |
| C08L 33/02 | (2006.01) | |
| C08K 5/15 | (2006.01) | |
| C08L 3/00 | (2006.01) | |
| A61L 17/10 | (2006.01) | |
| C08F 2/44 | (2006.01) | |
| A61L 15/62 | (2006.01) | |
| A61L 15/60 | (2006.01) | |

(52) U.S. Cl.
CPC . *C08F 2/44* (2013.01); *A61L 15/62* (2013.01); *A61L 15/60* (2013.01)
USPC ................. 524/556; 524/47; 524/51; 524/54; 524/110; 524/599

(58) Field of Classification Search
CPC ............. C08L 33/02; C08L 3/06; C08L 3/04; C08L 3/02; A61L 15/20; A61L 15/22; A61L 15/28; A61L 15/225
USPC .......................... 524/556, 599, 47, 51, 54, 110
See application file for complete search history.

(56) References Cited

U.S. PATENT DOCUMENTS

| | | | |
|---|---|---|---|
| 4,076,663 A | 2/1978 | Masuda et al. | |
| 4,131,576 A | 12/1978 | Iovine et al. | |
| 4,179,367 A | 12/1979 | Barthell et al. | |
| 4,286,082 A | 8/1981 | Tsubakimoto et al. | |
| 4,340,706 A | 7/1982 | Obayashi | |
| 4,587,308 A | 5/1986 | Makita et al. | |
| 4,857,610 A | 8/1989 | Chmelir et al. | |
| 4,893,999 A | 1/1990 | Chmelir et al. | |
| 5,340,853 A * | 8/1994 | Chmelir et al. | 524/56 |
| 5,409,771 A | 4/1995 | Dahmen et al. | |
| 5,610,220 A | 3/1997 | Klimmek et al. | |
| 5,672,633 A | 9/1997 | Brehm et al. | |
| 5,712,316 A | 1/1998 | Dahmen et al. | |
| 5,801,116 A * | 9/1998 | Cottrell et al. | 502/404 |
| 6,444,653 B1 | 9/2002 | Huppe et al. | |
| 6,620,889 B1 | 9/2003 | Mertens et al. | |
| 7,179,862 B2 | 2/2007 | Mertens et al. | |
| 7,407,912 B2 | 8/2008 | Mertens et al. | |
| 7,625,957 B2 | 12/2009 | Harren et al. | |
| 7,816,426 B2 | 10/2010 | Ahmed et al. | |
| 7,939,597 B2 | 5/2011 | Bub et al. | |
| 8,445,596 B2 | 5/2013 | Mertens et al. | |
| 2002/0156048 A1 | 10/2002 | Huppe et al. | |
| 2003/0027787 A1 | 2/2003 | Couture et al. | |
| 2003/0069359 A1* | 4/2003 | Torii et al. | 525/178 |
| 2003/0232965 A1 | 12/2003 | Bergeron | |
| 2004/0121905 A1* | 6/2004 | Ranganathan et al. | 502/402 |
| 2004/0157734 A1* | 8/2004 | Mertens et al. | 502/401 |

(Continued)

FOREIGN PATENT DOCUMENTS

| | | |
|---|---|---|
| DE | 2706135 A1 | 8/1978 |
| DE | 2840010 A1 | 6/1979 |

(Continued)

OTHER PUBLICATIONS

Michell et al; JACS, 1942, 64(3), 585-588.*

(Continued)

*Primary Examiner* — Karuna P Reddy
(74) *Attorney, Agent, or Firm* — Smith Moore Leatherwood LLP; Philip P. McCann; John P. Zimmer (57) ABSTRACT

The present invention generally relates to a method for the production of a superabsorbent composition comprising the process steps:

i. production of a hydrogel by radical polymerization of an aqueous monomer solution containing at least one monomer ii. drying the hydrogel to obtain a water-absorbing polymer structure iii. surface crosslinking of the water-absorbing polymer structure to obtain a surface-crosslinked water-absorbing polymer structure, and iv. incorporating a starch compound into the method.

The present invention also relates to a superabsorbent composition obtainable according to this method, a particulate superabsorbent composition and a composite, a sanitary article core and a sanitary item, furthermore chemical products and also the use of this superabsorbent composition in chemical products.

19 Claims, 1 Drawing Sheet

(56) References Cited

U.S. PATENT DOCUMENTS

| | | |
|---|---|---|
| 2004/0214499 A1 | 10/2004 | Qin et al. |
| 2006/0029782 A1 | 2/2006 | Harren et al. |
| 2006/0057389 A1 | 3/2006 | Reimann et al. |
| 2007/0066754 A1 | 3/2007 | Loeker et al. |
| 2007/0260357 A1 | 11/2007 | Issberner et al. |
| 2008/0221277 A1 | 9/2008 | Walden et al. |
| 2008/0262155 A1 | 10/2008 | Mertens et al. |
| 2008/0280128 A1 | 11/2008 | Furno et al. |
| 2009/0023006 A1 | 1/2009 | Bub et al. |
| 2009/0105389 A1 | 4/2009 | Walden et al. |
| 2009/0202805 A1 | 8/2009 | Fumo et al. |
| 2009/0227741 A1 | 9/2009 | Walden et al. |
| 2010/0035757 A1 | 2/2010 | Furno et al. |
| 2010/0036004 A1 | 2/2010 | Harren et al. |
| 2010/0209379 A1 | 8/2010 | Fumo et al. |
| 2011/0009272 A1 | 1/2011 | Wattebled et al. |
| 2011/0009841 A1 | 1/2011 | Ahmed et al. |
| 2011/0144294 A1 | 6/2011 | Bub et al. |

FOREIGN PATENT DOCUMENTS

| | | | |
|---|---|---|---|
| DE | 4418818 A1 | 1/1985 | |
| DE | 3503458 A1 | 8/1985 | |
| DE | 3544770 A1 | 6/1987 | |
| DE | 3713601 A1 | 11/1988 | |
| DE | 4020780 C1 | 8/1991 | |
| DE | 4244548 A1 | 7/1994 | |
| DE | 4333056 A1 | 3/1995 | |
| DE | 19518645 C1 | 9/1996 | |
| DE | 10125599 A1 | 11/2002 | |
| EP | 530438 A1 * | 3/1993 | ............. A61L 15/00 |
| EP | 0752892 B1 | 7/2001 | |
| GB | 2341866 A | 3/2000 | |
| JP | 57133142 A * | 8/1982 | |
| JP | 2002538275 A | 11/2002 | |
| WO | 9200108 A1 | 1/1992 | |
| WO | 9605234 A1 | 2/1996 | |
| WO | 9727884 A1 | 8/1997 | |
| WO | 9934843 A1 | 7/1999 | |
| WO | 0238614 A1 | 5/2002 | |
| WO | 02056812 A1 | 7/2002 | |
| WO | 2004037903 A2 | 5/2004 | |
| WO | 2004085481 A1 | 10/2004 | |
| WO | 2005011860 A2 | 2/2005 | |
| WO | WO 2005030279 A1 * | 4/2005 | |
| WO | 2006101271 A1 | 9/2006 | |

OTHER PUBLICATIONS

JP 57133142 A; Masuda et al; Aug. 1982; Abstract in English.*
English Translation of JP 57-133142 A; Aug. 1982.*
Composite Material, Wikipedia, 2005.*
English Translation of Preliminary Report on Patentability in PCT/EP2007/001712.
Roquette Pharma & Personal Care web page, Dextrins starch polymers—Monograph, copyright Jul. 2011, http://www.roquette-pharma.com/dextrins-starch-polymers-carbohydrate-food-ingredient-fiber-sources/#.
Roquette Pharma & Personal Care web page, Extra white maize starch—Monograph, copyright Jul. 2011, http://www.roquette-pharma.com/maize-starch-native-starch-diluent-disintegrating-tablets-disintegrant/#.
Roquette Pharma & Personal Care web page, Maize starch—Monograph, copyright Jul. 2011, http://www.roquette-pharma.com/maize-starch-filler-disintegration-diluent-tablets-capsules-powders/#.
Roquette Pharma & Personal Care web page, Potato Starch B—Monograph, copyright Jul. 2011, http://www.roquette-pharma.com/potato-starch-filler-diluent-tablets-capsules-disintegration/.
Roquette Pharma & Personal Care web page, Powdered NF Corn starches—Monograph, copyright Jul. 2011, http://www.roquette-pharma.com/corn-starch-native-starches-filler-binder-disintegrant-dusting-powder/.
Roquette Pharma & Personal Care web page, Starch 400L NF—Monograph, copyright Jul. 2011, http://www.roquette-pharma.com/excipient-starches-corn-starch-diluent-carrier-binder-dusting-powder/#.
Roquette Pharma & Personal Care web page, Wheat Starch TB—Monograph, copyright Jul. 2011, http://www.roquette-pharma.com/wheat-starch-excipient-diluent-tablets-capsules-disintegrant/#.

* cited by examiner

BIODEGRADABLE SUPERABSORBENT POLYMER COMPOSITION WITH GOOD ABSORPTION AND RETENTION PROPERTIES

This application is a national stage application under 35 U.S.C. 371 of international application No. PCT/EP2007/001712 filed 28 Feb. 2007, and claims priority to German Application No. DE 10 2006 009 579.0-43 filed 28 Feb. 2006, the disclosures of which are expressly incorporated herein by reference.

BACKGROUND

The present invention generally relates to a method for the production of a superabsorbent composition, a superabsorbent composition obtainable by said method, a particulate superabsorbent composition plus a composite, a sanitary article core and a sanitary article and furthermore chemical products, such as foams, shaped bodies, fibers, sheets, films, cables, sealing materials, liquid-absorbing sanitary articles, carriers for means to regulate plant and fungal growth, packaging materials, soil additives or building materials, each containing an absorbent composition and also the use of this superabsorbent composition in the chemical products.

Superabsorbers are water-insoluble, crosslinked polymers which are capable of absorbing large amounts of aqueous liquids, in particular body fluids, such as urine or blood, with swelling and the formation of hydrogels and of retaining them under pressure. Generally, this liquid absorption amounts to at least 10 times or even at least 100 times the dry weight of the superabsorber or the superabsorbent composition in water. As a result of these characteristic properties, these polymers are predominantly used in sanitary articles, such as babies' diapers, incontinence products or sanitary towels. A comprehensive overview of superabsorbers or superabsorbent compositions, their application, and their production is provided by F L Buchholz and A T Graham (editors) in "Modern Superabsorbent Polymer Technology", Wiley-VCH, New York, 1988.

Superabsorbers may be produced by means of the radical polymerization of acid-group-bearing, partially neutralized monomers in the presence of crosslinking agents. Here, the choice of the monomer composition, the crosslinking agents, the polymerization conditions and the processing conditions for the hydrogel obtained following the polymerization allows the production of polymers with different absorber properties.

Absorbent polymers substantially based on saccharides such as cellulose and starch have been known and are the subject of research today with the objective of improving suitability for use in diapers; these are described inter alia in WO 2004/085481 A1. In order to improve their absorption and retention properties, polysaccharides of this type are copolymerized with acrylic acid. Although this copolymerization did improve the absorption and retention properties of copolymers of this kind, the biodegradability of copolymers of this kind suffered with the use of this measure. In recent times, the trend has been increasingly toward the almost exclusive production of superabsorbers based on acrylic acid or acrylates since these loosely crosslinked, partially neutralized polyacrylates have the best absorption, retention and permeability properties compared to polysaccharides or polysaccharide-acrylate copolymers and, in particular in the form of surface or post-crosslinked superabsorbent polymers, are particularly suitable for the production of absorbent layers with a high filling of superabsorbers (generally with more than 50% of superabsorbers) which in turn are excellent for processing into sanitary articles, in particular female sanitary articles, babies' diapers and incontinence products, in order to obtain sanitary articles with excellent wearing and functional properties.

Unfortunately, these superabsorbent polymers, which are virtually exclusively based on acrylic acid or acrylates, have an inadequate level of biodegradability. In the light of the increasing environmental awareness of consumers requiring sanitary articles, environmental requirements for sanitary articles have increased considerably over recent years. However, more environmentally friendly sanitary articles may only be successfully marketed if their other functional properties are not noticeably worse than those of conventionally produced, and hence less environmentally friendly, sanitary articles.

An object of the present invention is to reduce or even overcome the drawbacks resulting from the prior art.

SUMMARY

One object of the present invention consists in improving the environmental friendliness of conventional sanitary articles by means of the provision of suitable superabsorbers without this significantly impairing their retention or absorption capacity and, if possible, their permeability. In this way, it is possible to alleviate or even avoid the phenomenon of gel blocking and the associate leakage even with cores or absorbent layers with a superabsorber content of more than about 50%.

Another object of the invention consists in providing a method for obtaining a superabsorber that improves the environmental friendliness of sanitary articles without significantly impairing their functionality.

A contribution to the achievement of at least part of these objects is made by a method for the production of a superabsorbent composition comprising the process steps:
  i. producing a hydrogel by the radical polymerization of an aqueous monomer solution containing at least one monomer
  ii. drying the hydrogel to obtain a water-absorbing polymer structure
  iii. surface crosslinking of the water-absorbing polymer structure to obtain a surface-crosslinked water-absorbing polymer structure
  iv. incorporating a starch compound in one or at least two or at least three or at least four or each of the following variants
   V1. in process step i. into the monomer solution
   V2. after process step i. and prior to process step ii. into the hydrogel
   V3. in process step ii.
   V4. after process step ii. and prior to process step iii. into the water-absorbing polymer structure
   V5. in process step iii
   V6. after process step iii onto the surface-crosslinked water-absorbing polymer structure.

In principle, every conceivable combination of the numbered variants V1 to V6 represents an embodiment of the method according to the invention. Each of the following combinations of the different variations, which are presented as numerical combinations, represents a preferred embodiment of the present invention: V1V2, V1V3, V1V4, V1V5, V1V6, V2V3, V2V4, V2V5, V2V6, V3V4, V3V5, V3V6, V4V5, V4V6, V1V2V3, V1V2V4, V1V2V5, V1V2V6, V1V3V4, V1V3V5, V1V3V6, V1V4V5, V1V4V6, V1V5V6, V2V3V4, V2V3V5, V2V3V6, V3V4V5, V3V4V6, V4V5V6, V1V2V3V4, V2V3V4V5, V3V4V5V6, V1V2V4V5V6, V1V2V3V5V6, V1V2V3V4V6, V1V2V3V4V5, V2V3V4V5V6, V1V3V4V5V6, wherein V1V4, V1V5, V1V6, V2V4, V2V5, V2V6 and V1V2V5 and V1V2V6 are examples of embodiments.

FIGURES

The foregoing and other features, aspects, and advantages of the present invention will become better understood with regard to the following description, appended claims, and accompanying drawings where:

DETAILED DESCRIPTION

The starch compound may be any starch compound which is known to a person skilled in the art and appears suitable for the present invention. Here, the term starch compound should be understood as starch per se and also starch derivatives. The incorporation of the starch compound may be performed in any form known to a person skilled in the art that appears suitable. For example, according to variant V1, the starch compound/monomer solution may be mixed in process step i. Here, it is possible on the one hand for the starch compound to be a water-soluble starch compound and the monomer solution to be an aqueous monomer solution. This method ensures that the incorporation of the starch compound into the monomer solution takes place as homogeneously as possible so that the starch compound is distributed as homogeneously as possible in the product of the polymerization of the aqueous monomer solution, which occurs in the form of a hydrogel. On the other hand, the starch compound may also be introduced into the monomer solution as a powder or powder suspension and this may then be brought to polymerization to obtain a hydrogel. The hydrogel obtained in this way generally has a water content in a range of from about 30 to about 80% by weight, or in a range from about 40 to about 70% by weight and occurs as an easily kneadable dough-like mass. According to the variant V2, this easily kneadable and grindable mass may also be very homogeneously distributed into the starch compound by kneading-in the starch compound powder. This kneading-in may be performed in conjunction with the grinding of the hydrogel.

In connection with the incorporation according to variant V3, it is advantageous to apply the starch compound to the already pre-comminuted hydrogel before or during the drying process. When this is done, improved adhesion of the starch compound, which in this case once again is present in powder form, may be achieved in that this is applied to the hydrogel to be dried or to the hydrogel undergoing drying in moistened form or combined with a binder, whereby the combination of moistening and application with a binder also represents an embodiment according to the invention.

In variant V4, a starch compound may be incorporated into the water-absorbent polymer which is already dried, generally ground and classified by screening. The powdery starch compound may be applied to the water-absorbing polymer either moistened or with a binder. Here, just as in connection with previous variant, it is advantageous for the moistening and the use of a binder to be employed together. In addition, in variant V4, it is possible first to apply the generally powdery starch compound in dry form to the water-absorbing polymer structure by mixing and to carry out the moistening and hence the improvement of adhesion in process step iii. in conjunction with the application of an aqueous surface crosslinking agent, for example an Al-sulfate-ethylene carbonate solution or an Al-sulfate-polyol solution, each of which are water-based.

In variant V5, the application of the generally powdery starch compound may be carried out in conjunction with the application of the surface crosslinking agent. This may be done, in the form of a solution, for example the above-mentioned aluminum-sulfate-ethylene carbonate or polyol solution, or, however, also by the application of an extremely finely ground surface crosslinking agent in solid form, such as solid aluminum sulfate. With the last named procedure, the solid surface crosslinking agent of the powdery starch compound after preliminary mixing of these two components, may be mixed with the water-absorbing polymer structure. Regardless of whether the surface crosslinking agents are applied as liquids or solids, this application is generally followed by thermal treatment, usually in a temperature range of from about 150 to about 300° C., often in a temperature range of from about 170 to about 250° C., in order to bring about the surface crosslinking.

According to variant V6, it is possible to incorporate the starch compound after the surface crosslinking or to the surface-crosslinked water-absorbing polymer structure. This may take place both with a moistened compound and with the aid of a binding agent to make the starch compound adhere to the surface-crosslinked water-absorbing polymer structure or by a combination of moistening and the use of a binding agent, preferably a polymeric binder. Generally, the application of the starch compound in variant V6 may be followed by a maturing step in which it is either slowly and carefully intermixed or subjected to mild temperature treatment or a combination of these two measures. Possible combinations of variants are V1V6, V4V6 and V2V6, whereby in V1 may be the starch compound with the properties of starch compound SI is used.

In connection with method according to the invention, one or more of the starch compound(s) may be water-soluble. Starch compounds are deemed to be water-soluble in particular if at least about 30 g of the starch compound may be dissolved in a liter of deionized water at a temperature of 20° C.

In addition, at least about 70% by weight, or at least about 80% by weight, or at least about 90% by weight of the starch compounds to have a particle size of less than about 100 μm, or less than about 75 μm or less than about 50 μm. The starch compounds may have weight averages of the particle sizes in a range from about 20 to about 80, or from about 25 to about 75, or from about 30 to about 70 μm, and for less than about 10% by weight of the particles to have a particle size of less than about 5 μm and for less than 10% by weight to have a particle size of more than about 90 μm.

The starch compound may have at least one, or at least two, or each of the following properties:
S1 a free absorption (FA) of at least about 9 g/g; or at least about 15 g/g, or at least about 18 g/g
S2 a retention (CRC) of at least about 7 g/g, or at least about 10 g/g, or at least about 12 g/g, or at least about 13 g/g, or at least about 12 g/g
S3 an absorption at pressure ($AAP_{0.3}$) of at least about 2 g/g, or at least about 3 g/g, or at least about 4 g/g, or at least about 4.5 g/g S4 an absorption at pressure ($AAP_{0.7}$) of at least about 2 g/g, or at least about 3 g/g, or at least about 4 g/g, or at least about 5 g/g.

Often, the absorption, retention and absorption at pressure of the starch compounds reach no more than about 25 to about 35 g/g. Starch compounds of this kind may be used in variant V1.

At least one first starch compound SI may be incorporated in the variants V1 or V2 and also in the variants V1 and V2. Starch compound SI may included starch-based compounds with a low amylose content, i.e. less than 60%, or less than 50%, or less than 30% amylose, in each case based on the total starch compound. In addition, starch compounds SI may be based on potato starch. Starch compounds SI may be at least partially carboxyalkylated. Here, suitable alkyl compounds may be lower alkyl compounds such as methyl, ethyl, propyl and butyl, whereby methyl and ethyl are preferred and methyl is particularly preferred. Preferably, starch compound SI is at least about 10%, or at least about 50%, or at least about 75% carboxyalkylated, in each case based on the starch compound SI. Starch compounds SI may be based on potato starch, contain less than about 20% amylose and are more than about 75% carboxymethylated.

In addition to the first starch compound SI, at least one further starch compound SII may be incorporated in a variant different from the variants V1 and V2. This at least one further starch compound SII may be incorporated in variant 5, i.e. in process step iii, of the surface crosslinking. In the method according to the invention, the first starch compound SI and the further starch compound SII may differ from each other in at least one feature. The first starch compound SI and the further starch compound SII may differ from each other in at least one, or at least two, or in each of the following features:
D1 in the free absorption (FA), here preferably by a difference of at least about 0.1, or at least about 1, or at least about 5, or at least about 15 g/g
D2 in the retention (CRC), here by a difference of at least about 0.1, at least about 1, or at least about 3, or at least about 6 g/g
D3 in the pH value, here by a difference of at least about 0.1, or at least about 1, or at least about 3, or at least about 6, and
D4 in the chemical composition, in the degree of carboxyalkylation or the amylose content, or in the degree of carboxyalkylation and the amylose content
The starch compounds S1 and SII may differ in the features D1 to D3.

In addition, the starch compound SII may have at least one of the following properties
d1 a free absorption (FA) of less than about 9 g/g, less than about 8 g/g, or at least about 6 g/g;
d2 a retention (CRC) of at least about 7 g/g, less than about 6 g/g, or less than 5.5 g/g, or
d3 a pH value in the range from about 3 to less than 9, or from about 4 to about 8.5, or from about 5 to about 8.

The starch compound SII may have at least the features d1 or d2, in each case in combination with d3.

In addition, the starch compound SII may have a higher amylose content than the starch compound SI. For example, the starch compound SII may comprise at least about 60%, or at least about 65%, or at least about 70% amylose. In addition, the starch compound SII may also be used on its own, i.e. as the sole starch compound.

In general, the starch compounds may be used in the method according to the invention in an amount of a maximum of about 30% by weight, or a maximum of about 20% by weight, or a maximum of about 15% by weight, or a maximum of about 10% by weight, in each case based on the monomer used. In the event that more than one starch compound, in particular a first starch compound SI and at least one further starch compound SII are used, the above maximum starch compound amounts also retain their validity, whereby these are then based on all starch compounds.

The further starch compound may be incorporated in at least one of the variants V3 to V6. This incorporation may also take place in a water-absorbing polymer structure in which one first starch compound SI or more first starch compounds SIa, SIb have already been incorporated. However, there is also an embodiment of the method conceivable according to the invention in which one or at least two starch compounds SII are incorporated into one of the variants V3 to V6.

In addition, the monomer solution may have a monomer content in the range from about 15 to about 35% by weight, or in the range from about 20 to about 30% by weight, or in a range from about 22.5 to about 27.5% by weight, in each case based on the monomer solution. This procedure is advantageous if one or more starch compounds according to variant V1 are incorporated into the monomer solution.

In addition, the starch compound may have a solution viscosity according to the method specified here in a range from about 5000 to about 300000 mPas, or in a range from about 10000 to about 100000 mPas, or in a range from about 20000 to about 50000 mPas.

In addition, the starch compound may comprise less than about 10% by weight, or less than about 7% by weight, or less than about 3% by weight of cyclic or branched polysaccharides.

Starch compounds may include those that may be obtained from the Roquette GmbH company, Germany, under the trade names Tackidex®, for example Tackidex® 009 or Tackidex® Q 106, Eurylon®, for example Eurylon® 7, Floralys®, for example Floralys® 380, or the products T 547, T 548 or T 549.

The superabsorbent composition may have at least one, or at least two, or each of the following properties
Z1 a retention (CRC) of at least about 25 g/g, or at least about 27 g/g, or at least about 29 g/g
Z2 an absorption at pressure ($AAP_{0.7}$) of at least about 15 g/g, or at least about 17 g/g, or at least about 19 g/g
Z3 a permeability (SFC) of at least about $20 \times 10^{-7}$ $cm^3$ sec/g, or at least about $24 \times 10^{-7}$ $cm^3$ sec/g, or at least about $28 \times 10^{-7}$ $cm^3$ sec/g, and
Z4 a biodegradability determined according to the test described here after 28 days of at least about 25%, or at least about 35%, or at least about 45%.

All the combinations of numbers Z1 to Z4 that are possible here represent embodiments of the method according to the invention, such as combinations Z1Z2, Z1Z3, Z1Z4, Z1Z2Z4, Z1Z2Z3 and Z2Z3Z4, or the combination with Z4. This includes Z4Z1, Z4Z2 and Z4Z3 of the properties of the superabsorbent compositions obtainable by means of the method according to the invention. Often, absorption at pressure values of 30 to 50 g/g and retention values of 50 to 70 g/g and permeability values of $90 \times 10^{-7}$ $cm^3$ sec/g to $110 \times 10^{-7}$ $cm^3$ sec/g are not exceeded as maximum values, whereby a biodegradability value of a maximum of 75 to 95% is also often not exceeded as an upper limit.

According to another embodiment of the superabsorbent composition according to the invention and the method for its production, use may be made of a binder or polymeric binder that is different from the water-absorbing polymer structure and that is contained in the composition produced according to the invention. In principle, appropriate polymeric binders are all polymeric binders that are known to a person skilled in the art for the purpose of the fixation of the starch compound and appear suitable. These binders include thermoplastic polymers. In this connection, reference is made to the thermoplastic polymers described in WO 2005/011860. Polymeric binders of this kind have a molecular weight that is determined by GPC (gel permeation chromatography) and absolutely detectable by light scattering in a range from 1000 to 100,000, or from 2000 to 50,000, or from 3000 to 15,000 g/mol. In addition, polymeric binders of this kind may contain two or more OH groups. Examples of suitable polymeric binders are polyalkylene glycols, such as polyethylene glycol, polypropylene glycol, whereby polyethylene glycol and in particular a polyethylene glycol with a molecular weight in a range from 5000 to 15,000 g/mol. The molecular weights mentioned here relate in each case to the weight average of the molecular weight.

Polymer structures according to the invention are fibers, foams, or particles. The same also applies to the superabsorbent composition according to the invention.

Polymer fibers according to the invention may be dimensioned in such a way that they may be incorporated in or as yarns for textiles and also directly in textiles. The polymer structures may be present in the form of polymer fibers to have a length in a range of from about 1 to about 500 mm, or from about 2 to about 500 mm, or from about 5 to about 100 mm, and a diameter in a range of from about 1 to about 200 denier, or from about 3 to about 100 denier, or from about 5 to about 60 denier.

Polymer particles according to the invention may be dimensioned in such a way that they have an average particle size according to ERT 420.2-02 in a range of from about 10 to about 3000 µm, or from about 20 to about 2000 µm, or from about 150 to about 850 µm. Hereby, a proportion of polymer particles may have a particle size in a range of from about 300 to about 600 µm to be at least 30% by weight, or at least 40% by weight, or at least 50% by weight based on the total weight of the post-crosslinked water-absorbing polymer particles.

The water-absorbing polymer structures used according to the invention, may be based on
  ($\alpha 1$) 20-99.999% by weight, or 55-98.99% by weight, or 70-98.79% by weight of polymerized, ethylenically unsaturated, acid-group-containing monomers or the salts thereof or polymerized, ethylenically unsaturated monomers comprising a protonated or quaternated nitrogen or mixtures thereof whereby mixtures comprising at least ethylenically unsaturated acid-group-containing monomers, such as acrylic acid;
  ($\alpha 2$) 0-80% by weight, or 0-44.99% by weight, or 0.1-44.89% by weight of polymerized, monoethylenically unsaturated monomers which are copolymerisable with ($\alpha 1$)
  ($\alpha 3$) 0.001-5% by weight, or 0.01-3% by weight, or 0.01-2.5% by weight of one or more crosslinking agents
  ($\alpha 4$) 0 to 30% by weight, or 0 to 5% by weight, or 0.1 to 5% of a water-soluble polymer
  ($\alpha 5$) 0 to 20% by weight, or 2.5 to 15% by weight, or 3 to 10% of water
  ($\alpha 6$) 0 to 20% by weight, or 0 to 10% by weight, or 0.1 to 8% of one or more additives wherein the sum of the weight quantities ($\alpha 1$) to ($\alpha 6$) amounts to 100% by weight.

The monoethylenically unsaturated acid-group-containing monomers ($\alpha 1$) may be partially or fully neutralized. The monoethylenically unsaturated acid-group-containing monomers are at least about 25 mol % neutralized, or at least 50 mol % neutralized, or 50-80 mol % neutralized. In this connection, reference is made to DE 195 29 348 A1 the disclosure of which is cited here as a reference. The neutralization may also occur partially or fully after the polymerization. In addition, neutralization may occur with alkali metal hydroxides, alkaline earth metal hydroxides, ammonia and carbonates and bicarbonates. Apart from these, any other base which forms a water-soluble salt with the acid is also conceivable. Mixed neutralization with different bases is also conceivable. Neutralization with ammonia and alkaline metal hydroxides is preferred, particularly preferably with sodium hydroxide and ammonia.

Furthermore, the free acid groups may predominate in a polymer so that this polymer has a pH value within the acidic range. This acidic water-absorbing polymer may be at least partially neutralized by a polymer with free basic groups, such as amine groups, which is basic compared to the acidic polymer. These polymers are referred to in literature as "mixed bed ion-exchange absorbent polymers" (MBIEA polymers) and are disclosed inter alia in WO 99/34843 A1. The disclosure in WO 99/34843 A1 is cited here as a reference. As a rule, MBIEA polymers represent a composition which comprises, on the one hand, basic polymers which are able to exchange anions and, on the other hand, a polymer which is acidic compared to the basic polymer which is able to exchange cations. The basic polymer comprises basic groups and is typically obtained by the polymerization of monomers which carry basic groups or groups which may be converted into basic groups. These monomers are yet more those that comprise primary, secondary or tertiary amines or the corresponding phosphines or at least two of the aforementioned functional groups. This group of monomers includes in particular ethyleneamine, allylamine, diallylamine, 4-aminobutene, alkyloxycyclene, vinylformamide, 5-aminopentene, carbodiimide, formaldacine, melamine and the like plus their secondary or tertiary amine derivatives.

Ethylenically unsaturated acid-group-containing monomers ($\alpha 1$) include those compounds named as ethylenically unsaturated acid-group-containing monomers ($\alpha 1$) in WO 2004/037903 A2 which is cited here as a reference. Ethylenically unsaturated acid-group-containing monomers ($\alpha 1$) include acrylic acid and methacrylic acid.

According to one embodiment of the present invention, water-absorbing polymer structures are used in which the monoethylenically unsaturated monomers ($\alpha 2$) which are copolymerisable with ($\alpha 1$) are acrylamides and methacrylamides or vinylamides.

Apart from acrylamide and methacrylamide, (meth)acrylamides include alkyl-substituted (meth)acrylamides or aminoalkyl-substituted derivatives of (meth)acrylamide such as N-methylol(meth)acrylamide, N,N-dimethylamino(meth)acrylamide, dimethyl(meth)acrylamide or diethyl(meth)acrylamide. Possible vinylamides are, for example, N-vinylamides, N-vinylformamides, N-vinylacetamides, N-vinyl-N-methylacetamides, N-vinyl-N-methylformamides, vinylpyrrolidone.

According to another embodiment of the present invention, water-absorbing polymer structures are used in which the monoethylenically unsaturated monomers ($\alpha 2$) which are copolymerizable with ($\alpha 1$) are water-soluble monomers. In this connection, alkoxypolyalkylenoxide(meth)acrylates such as methoxypolyethyleneglycol(meth)acrylates may be used.

Monoethylenically unsaturated monomers ($\alpha 2$) which are copolymerisable with ($\alpha 1$) may include water-dispersible monomers. Water-dispersible monomers are acrylic acid esters and methacrylic acid esters, such as methyl(meth)acrylate, ethyl(meth)acrylate, propyl(meth)acrylate or butyl(meth)acrylate.

The monoethylenically unsaturated monomers (α2) which are copolymerisable with (α1) also include methylpolyethyleneglycol-allylether, vinyl acetate, styrene and isobutylene.

Crosslinking agents (α3) include those compounds named in WO 2004/037903 A2 as crosslinking agents (α3). Of these crosslinking agents, water-soluble crosslinking agents may be used. These include N,N'-methylenebisacrylamide, polyethylene glycol di(meth)acrylates, triallylmethylammonium chloride, tetraallylammonium chloride and allylnonaethylene glycol acrylate made with 9 mol ethylene oxide per mol acrylic acid.

As water soluble polymers (α4), water soluble polymerizates such as partly or fully saponified polyvinyl alcohol, polyvinylpyrrolidone, polyglycols or polyacrylic acids may be included, or be polymerized into, the absorbent polymer structures. The molecular weight of these polymers is not critical, as long as they are water soluble. Water soluble polymers include polyvinyl alcohols. The water soluble polymers, may be synthetic like polyvinyl alcohol, or may also serve as graft basis for the monomers to be polymerized.

As additives (α6) suspension agents, odor binders, surface-active agents or antioxidants as well as those additives used for the preparation of the polymer structures (initiators etc.) may be contained in the polymer structures.

According to the invention, water-absorbing polymer structures may include polymers that are obtained by a method comprising the following process steps:
a) radical polymerization of acid-group-containing ethylenically unsaturated, optionally partially neutralized monomers in the presence of a crosslinking agent with the formation of a hydrogel
b) optionally comminution of the hydrogel
c) drying of the optionally comminuted hydrogel to obtain water-absorbing polymer structures
d) optionally grinding of the absorbing polymer structure obtained in this way and screening to a desired particle size fraction
e) optionally, further surface modifications of the water-absorbing polymer structures obtained in this way Suitable types of mixing apparatus for surface modification and also for the application of the odor binder or at least one of its components are Peterson-Kelley mixers, DRAIS turbulence mixers, Lödige mixers, Ruberg mixers, screw mixers, pan mixers and fluidized bed mixers plus continuous vertical mixers in which the polymer structure is mixed at a high frequency by means of rotating knives (Schugi mixers).

The radical polymerization carried out in process step a) may be out in an aqueous solution, whereby, in addition to water, this aqueous solution preferably contains as a solvent
(α1) the ethylenically unsaturated acid-group-containing monomers or the salts thereof, whereby acrylic acid may be used as an acid-group-containing monomer
(α2) optionally monoethylenically unsaturated monomers which are copolymerisable with (α1)
(α3) the crosslinking agent
(α4) optionally a water-soluble polymer, and
(α6) optionally one or more additives.

Ethylenically unsaturated acid-group-containing monomers (α1), monoethylenically unsaturated monomers (α2) that are copolymerizable with (α1), as crosslinking agents (α3), as water-soluble polymers (α4) and as additives (α6) may include those compounds which were mentioned at the beginning in connection with the polymer structures according to the invention as ethylenically unsaturated acid-group-containing monomers (α1), as monoethylenically unsaturated monomers (α2) which are copolymerisable with (α1), as crosslinking agents (α3), as water-soluble polymers (α4), and as additives (α6).

The water-absorbing polymer structures may be produced from the aforementioned monomers, comonomers, crosslinking agents, water-soluble polymers, and additives using different types of polymerization. Examples to be mentioned in this context are bulk polymerization that may be carried out in kneader reactors such as extruders, solution polymerization, spray polymerization, inverse emulsion polymerization, or inverse suspension polymerization.

Solution polymerization may be carried out in water as a solvent. Solution polymerization may be carried out continuously by polymerization on a belt conveying the reactant, as disclosed in DE 35 44 770 A1, or discontinuously. Known from the prior art is a broad spectrum of possible variations to the reaction conditions such as the temperatures, type and quantity of the initiators and the reaction solution. Typical methods are described in the following patents: U.S. Pat. No. 4,286,082, DE 27 06 135, U.S. Pat. No. 4,076,663, DE 35 03 458, DE 35 44 770, DE 40 20 780, DE 42 44 548, DE 43 23 001, DE 43 33 056, DE 44 18 818.

As is generally usual, polymerization is triggered by an initiator. All initiators that form radicals under polymerization conditions usually used for the production of superabsorbers may be used as initiators for the initiation of the polymerization. The initiation of polymerization by exposing the polymerisable aqueous mixture to electron beams is also possible. However, polymerization may also be triggered in the absence of initiators of the aforementioned type by exposure to high-energy radiation in the presence of photoinitiators. Polymerization initiators may be contained dissolved or dispersed in a solution of monomers according to the invention. Possible initiators are all compounds which break down into radicals known to a person skilled in the art. These include in particular those initiators which have already been mentioned in WO 2004/037903 A2 as possible initiators.

A redox system comprising hydrogen peroxide, sodium peroxodisulfate, and ascorbic acid may be used to produce the water-absorbing polymer structures.

Inverse suspension and emulsion polymerization may also be used to produce the polymer structures. According to these processes, an aqueous, partially neutralized solution of monomers (α1) and (α2), optionally containing water-soluble polymers and additives, is dispersed in a hydrophobic organic solvent with the aid of protective colloids and/or emulsifiers and polymerization is started by radical initiators. The crosslinking agents are either dissolved in the monomer solution and are added together with this or separately and optionally during the polymerization. Optionally, a water-soluble polymer (α4) is added as a graft basis via the monomer solution or by direct addition into the oil phase. Then, the water is removed from the mixture azeotropically and the polymer filtered off.

Furthermore, during solution polymerization and inverse suspension and emulsion polymerization, the crosslinking may be carried out by copolymerization of the polyfunctional crosslinking agent dissolved in the monomer solution and/or by the reaction of suitable crosslinking agents with functional groups of the polymers during the polymerization steps. The methods are, for example, described in the publications U.S. Pat. No. 4,340,706, DE 37 13 601, DE 28 40 010 and WO 96/05234 A1 and the corresponding disclosure is cited here as a reference.

The hydrogels obtained with solution polymerization or inverse suspension and emulsion copolymerization in process step a) are dried in process step c).

However, it is preferred, particularly in the case of solution polymerization, prior to drying, for the hydrogels to be first comminuted in an additional process step b). This comminution is carried out using comminution equipment known to a person skilled in the art, such as a chopping knife (see DE 195 18 645 C1) or, for example, a meat grinder which may be positioned downstream of the chopping knife.

The hydrogel may be dried in suitable dryers or furnaces. Examples cited include drum-type furnaces, fluidized-bed dryers, disk dryers, paddle dryers, or infrared dryers. The drying of the hydrogel in process step c) may be performed to a water content of 0.5 to 25% by weight or from 1 to 10% by weight, whereby the drying temperatures are usually in a range of from about 100 to about 200° C.

In particular when they were obtained by solution polymerization, the dried water-absorbing polymer structures obtained in process step c) may be ground again in a further process step d) and screened to the desired grain size mentioned at the start. The grinding of the dried water-absorbing polymer structures may be carried out in suitable mechanical comminution equipment, such as for example a ball mill.

Following the drying of the hydrogels and after the optionally performed further treatment of the dried water-absorbing polymer structures, their surface area may be modified in a further process step e). This may be done by means of a metal salt or with a combination of the metal salt and a metal oxide or another modifying agent, whereby the substances above may be applied as an aqueous solution or as a solid. The treatment may be performed on both the water-absorbing polymer structures and the superabsorbent composition already containing the odor binder.

Here, surface post-crosslinking is mentioned as a measure in which the dried polymer structure or even the still undried, but already comminuted, hydrogel is brought into contact with a organic, chemical surface post-crosslinking agent. In particular if it is not liquid under the post-crosslinking conditions, the post-crosslinking agent is brought into contact with the polymer particles or the hydrogel by means of a solvent. Here, the solvents used may be water, organic solvents miscible with water, such as, for example, methanol, ethanol, 1-propanol, 2-propanol or 1-butanol or mixtures of at least two of these solvents, whereby water may be used. Furthermore, the post-crosslinking agent may be contained in the solvent or solvent mixture in a quantity in a range from about 5 to about 75% by weight, or from about 10 to about 50% by weight, or from about 15 to about 40% by weight based on the total weight of the solvent or solvent mixture.

In the method according to the invention, the polymer structure or the comminuted hydrogel may be brought into contact with the solvent or solvent mixture containing the post-crosslinking agent by mixing the solvent or solvent mixture thoroughly with the polymer structure.

Suitable mixers for the mixing are, for example, Patterson-Kelley mixers, DRAIS turbulence mixers, Lödige mixers, Ruberg mixers, screw mixers, pan mixers and fluidized-bed mixers plus continuous vertical mixers in which the polymer structure is mixed at high speed by means of rotating knives (Schugi mixers).

In the method according to the invention, during the post-crosslinking, the polymer structure may be brought into contact with a maximum of about 20% by weight, or a maximum of about 15% by weight, or with a maximum of about 10% by weight, or with a maximum of about 5% by weight of solvent, such as water.

In the case of polymer structures in the form of approximately spherical particles, the bringing-into contact may be effected in such a way that only the outer region, but not the inner region, of the particulate polymer structures is brought into contact with the solvent or mixer and hence with the post-crosslinking agent.

The post-crosslinking agents used in the method according to the invention should be understood to be compounds comprising at least two functional groups that may react with functional groups of a polymer structure in a condensation reaction (=condensation crosslinking agents), in an addition reaction or in a ring-opening reaction. The post-crosslinking agents in the method according to the invention may include those cited in WO 2004/037903 A2 as crosslinking agents of cross-linker class II.

Of these compounds, condensation crosslinking agents included as post-crosslinking agents are, for example, diethylene glycol, triethylene glycol, polyethylene glycol, glycerol, polyglycerol, propylene glycol, diethanolamine, triethanolamine, polyoxypropylene, oxyethylene/oxypropylene block copolymers, sorbitan fatty acid esters, polyoxyethylenesorbitan fatty acid esters, trimethylolpropane, pentaerythritol, polyvinyl alcohol, sorbitol, 1,3-dioxolan-2-one (ethylene carbonate), 4-methyl-1,3-dioxolan-2-one (propylene carbonate), 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one and particularly preferably 1,3-dioxolan-2-one.

When the polymer structures or the hydrogels have been brought into contact with the post-crosslinking agent or with the fluid containing the post-crosslinking agent, they are heated to a temperature within a range of from about 50 to about 300° C., or from about 75 to 275° C., or from about 150 to about 250° C. so that the outer region of the polymer structures is more extensively crosslinked than the inner region (=post-crosslinking). The duration of the heat treatment is restricted by the risk that the desired property profile of the polymer structures will be destroyed as a result of the action of the heat.

Furthermore, a superabsorbent composition obtained according to the method according to the invention makes a contribution to the achievement of at least one object of the present invention. This is particularly the case when this composition comprises the Z-properties (Z1 to Z4) in the variations described above.

In addition, a contribution to the achievement of at least one of the objects according to the invention is made by a particulate superabsorbent composition containing
- a crosslinked inner region based on partially neutralized acrylic acid within a range of about 70 to about 95% by weight based on the superabsorbent composition
- an outer region which is more strongly crosslinked than the inner region surrounding this inner region at least partially
- whereby at least one starch compound is incorporated into the superabsorbent composition in a quantity within a range of at least about 1% by weight based on the superabsorbent composition
- whereby the superabsorbent composition possesses at least one of the following properties
    z1 a retention (CRC) of at least about 25 g/g, or at least about 27 g/g, or at least about 29 g/g
    z2 an absorption at pressure ($AAP_{0.7}$) of at least about 15 g/g, or at least about 17 g/g, or at least about 19 g/g
    z3 a permeability (SFC) of at least about $20 \times 10^{-7}$ cm$^3$ sec/g, or at least about $24 \times 10^{-7}$ cm$^3$ sec/g, or at least about $28 \times 10^{-7}$ cm$^3$ sec/g z4 a biodegradability determined according to the test described here after 28 days of at least about 25%, or at least about 35%, or at least about 45%.

The superabsorbent composition according to the invention described in the above paragraph may comprise at least partially a core-shell structure, whereby the generally more strongly crosslinked outer region due to the post-crosslinking forms the shell. In connection with preferred embodiments, reference is made to the statements above relating to Z1 to Z4. The same applies to the particle sizes of the starch compound(s) incorporated in the composition.

The starch compound may be incorporated in the inner region. This should take place extremely homogeneously. In a further embodiment of the superabsorbent composition, a starch compound is incorporated in the outer region. Furthermore, in one superabsorbent composition according to the invention, a further starch compound SII different from a first starch compound SI incorporated in the inner region is incorporated in the outer region. Once again, reference is made to the statements relating to the different starch compounds SI and SII. The superabsorbent composition preferably has an average particle size within the range from about 200 to about 650 µm, whereby fewer than about 5% of the particles have diameters below about 150 µm and above about 850 µm respectively. This is generally achieved by screening with screens with mesh sizes of about 150 µm and about 850 µm.

A further contribution to the achievement of the objects described at the start is provided by a composite containing the superabsorbent composition according to the invention and a substrate. Here, the superabsorbent composition according to the invention and the substrate may be firmly bonded to each other. Substrates may be sheets made of polymers, such as for example, polyethylene, polypropylene or polyamide, metals, non-wovens, fluff, tissues, woven materials, natural, or synthetic fibers or other foams. Furthermore, the composite may comprise at least one region which contains the superabsorbent composition according to the invention in a quantity in a range from approximately 15 to 100% by weight, or from approximately 30 to 100% by weight, or from approximately 50 to 99.99% by weight, or from approximately 60 to 99.99%, or from approximately 70 to 99% by weight, based in each case on the total weight of the relevant region of the composite, whereby this region measures at least $0.01\ cm^3$, or at least $0.1\ cm^3$, or at least $0.5\ cm^3$.

One embodiment of the composite according to the invention is a flat composite such as that described in WO 02/056812 A1 as "absorbent material". The content of the disclosure in WO 02/056812 A1, in particular with regard to the precise structure of the composite, the weight per unit area of its components and its thickness is introduced here as a reference and forms part of the disclosure of the present invention.

A further contribution to the achievement of the objects described at the beginning is made by a method for the production of a composite, whereby the superabsorbent composition according to the invention and a substrate and optionally an additive are brought into contact with each other. Substrates may include the substrates already mentioned above in connection with the method according to the invention.

A contribution to the achievement of the objects described at the beginning is also made by a composite obtained according to the above-described method, whereby this composite preferably possesses the same properties as the above-described composite according to the invention.

According to one aspect of the present invention, the composite is embodied as a sanitary article core which, in each case based on the sanitary article core, comprises at least about 30% by weight, or at least about 50% by weight, or at least about 70% by weight of the water-absorbing composition according to the invention and at least about 1% by weight, or at least about 5% by weight, or at least about 10% by weight of the substrate and optionally further conventional additives or adhesives, whereby the sum of the percents by weight of the individual components contained in the sanitary article core amounts to 100% by weight. Substrate in connection with the sanitary article core may include materials used to fix the superabsorbent composition according to the invention that are generally present in the form of particles. These may be fibers or knitted materials or woven material and meshes. It is also possible for the superabsorbent composition which is, for example, present in the form of a powder and hence in particulate form, to be bonded to the substrate by an adhesive such as a glue. Similarly, in one embodiment, the substrate is embodied so that the superabsorbent composition is accommodated in a recess in the substrate. Usual additives also incorporated in the sanitary article core are, for example, substances, cosmetic substances which improve skin compatibility, disinfectants, antimicrobial substances, and the like.

In another aspect, the present invention relates to sanitary articles comprising a liquid-permeable top layer, a liquid-impermeable bottom layer and a composite according to the invention arranged between the top layer and the bottom layer. The sanitary articles in question are women's sanitary articles, adult incontinence products, and diapers for infants, babies and small children. The sanitary article may contain a sanitary article core as described above. In principle, the liquid-permeable top layer may comprise all woven materials, bonded and knitted fabrics known to a person skilled in the art for this purpose and which appear suitable which generally comprise cellulose or cellulose derivatives which are optionally bonded to plastics such as polypropylene or polyethylene. Also used as liquid-impermeable bottom layers are non-wovens familiar in industry to a person skilled in the art, generally also made of a cellulose or cellulose derivative, mat, stitched fabric, or knitted fabric, whereby this is generally sealed with a plastic layer, generally made of polypropylene or polyethylene.

A further contribution to the achievement of the objects described at the beginning is made by chemical products containing the superabsorbent compositions according to the invention or a composite according to the invention. Preferred chemical products are in particular foams, shaped bodies, fibers, sheets, films, cables, sealing materials, liquid-absorbing sanitary articles, in particular diapers and sanitary towels, carriers for means to regulate plant and fungal growth or pesticides, additives for building materials, packaging materials, or soil additives.

The use of the polymer structures according to the invention or the composite according to the invention in chemical products, such as in the aforementioned chemical products, in particular in sanitary articles such as diapers or sanitary towels, and the use of the superabsorbent particles as carriers for means to regulate plant and fungal growth or pesticides also make a contribution to the achievement of the objects described at the beginning. When used as carriers for means to regulate plant and fungal growth or pesticides, the means to regulate plant and fungal growth or pesticides may be released over a period controlled by the carrier.

The invention will now be described with reference to non-limiting examples.

Test Methods

General

Insofar as no other test methods are specified below, test methods that are generally known and usual for a person skilled in the art are used, whereby in particular the test methods of the EDANA (European Diaper and Nonwoven Association) are used—these are generally referred to as "ERT methods".

Retention

Retention was determined as CRC (Centrifuge Retention Capacity) according to ERT 441-2-02 on the entire size fraction, whereby absorption was carried out for 30 minutes directly followed by centrifuging for 3 minutes.

Absorption

Absorption at pressure was determined as AAP (Absorption at Pressure) according to ERT 442-2-02 on the entire size fraction. The numerical subscripts 0.3 and 0.7 indicate the respective pressures in psi at which absorption was measured. FA (Free Absorption) was determined according to ERT 442-2-02 on the entire size fraction, whereby in deviation from the method described therein, no pressure was exerted by omitting the corresponding weights.

Permeability

Permeability was determined as SFC (Saline Flow Conductivity) according to EP 0 752 892 B1 on the entire size fraction.

Acquisition Time and Liquid Distribution

Figure 1:
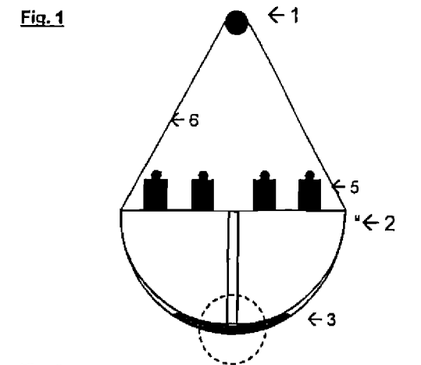
FIG. 1 shows a side section through the measuring equipment.
Figure 2:
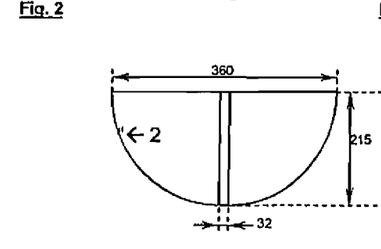
FIG. 2 shows the dimensions of the measuring device in a front view in mm.
Figure 3:
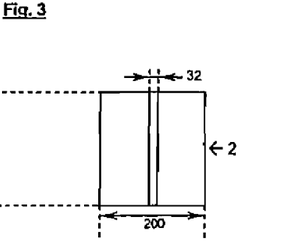
FIG. 3 shows the dimensions of the measuring device in a side view in mm.
Figure 4:
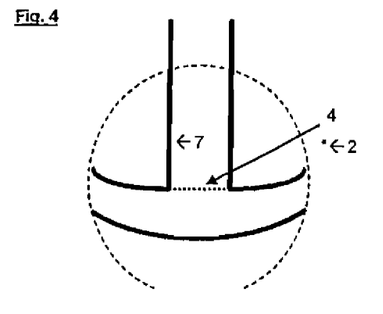
FIG. 4 shows a detail view of insert 2 of FIG. 1.

The measuring equipment for the determination of the acquisition time and liquid distribution of the cores is shown schematically in FIGS. 1 to 4. FIG. 1 shows a side section through the measuring equipment in which an insert 2 made of transparent plexiglass imitating in principle the buttocks of a person wearing a sanitary article is held on a suspension 1 embodied as a laboratory rod over a 200 mm wide approximately 1 mm thick, inflexible and smooth plastic film 6. The insert 2 is substantially a semicircle with a smooth surface with a central channel 7 which, as shown in a detail view in FIG. 4 has a screen 4 on its lower opening. The middle of the core 3 shown in the overview is located below the lower opening of the channel 7. The insert 2 is then loaded with the weights 5 provided for the measurements. The test liquid is poured into the measuring device through the upper opening of the channel 7. FIGS. 2 and 3 show the dimensions of the measuring device in a front view and side view in mm.

The core, with a length of 300 mm and a width of 120 mm, was weighed, placed in the body-shaped test apparatus and loaded with 9 kg. Then, 60 g of a 0.9% aqueous sodium chloride solution colored with 5 ml/l acid fuchsine stock solution (10.0 g of acid fuchsine solution was added to 1 l of a 0.9% sodium chloride solution and the pH value of the solution set at 6.0 by adding 0.3% aqueous NaOH) was added three times with an interval of 20 minutes by means of a measuring cylinder through the opening of the test apparatus. A stopwatch was used to measure the seepage time from the start of the addition of the test liquid until it had completely seeped away. Each addition of the test liquid was followed by a waiting period of 20 minutes. Then, the weights were removed. The liquid distribution was determined after the expiry of each 20-minute interval. For this, the diffusion of the liquid in the length of the core was measured.

Viscosity

The viscosity of the starches was determined at 20° C. with a Brookfield viscosimeter in a 6% aqueous solution.

pH Value

The pH value was determined in a 3% aqueous solution at 20° C.

Particle Size

With water-absorbing polymers and the superabsorbent compositions using screen analysis and evaluation according to ERT 420.02-02. In the case of starch compounds with a Beckmann Coutler LS particle sizer. The MMPSD (weight average of the particle size) was obtained from one application with semi-logarithmic scaling at 50% (see EP 0 304 319 B1).

Biodegradability

This was determined using the modified Sturm test according to Annex V to Directive 67/548/EEC for a period of 28 days.

EXAMPLES

Starting Materials

Freshly purified starting materials were used. In addition, the following commercially available starch compounds listed in Table 1 made by the company Roquette GmbH, Germany were also used.

TABLE 1

| Type | FA [g/g] | CRC [g/g] | $AAP_{0.3}$ [g/g] | $AAP_{0.7}$ [g/g] | Viscosity [mPa s] | Particle size [μm] <10 MMPSD >100 | | | pH value |
|---|---|---|---|---|---|---|---|---|---|
| 1 | 18.7 | 13.8 | 5.0 | 5.4 | 30,000 | | | % | 9-11.5 |
| 2 | 1.3 | 0.8 | | | | | | % | 5-7 |
| 3 | 5.7 | 5.2 | | | | | | % | 5-7 |
| 4 | 4.1 | 3.5 | | | | | | % | 5-7 |

Type 1 = Water-soluble carboxymethylated potato starch with the trade name Tackidex ® Q106
Type 2 = Water-soluble maize starch with an amylose content of 70% with the trade name Eurylon ® 7
Type 3 = Water-soluble wheat starch with the trade name Floralys ® 380
Type 4 = Water-soluble maize starch with the trade name Tackidex ® 009

Example 1

Production of a Non-Post-Crosslinked Water-Absorbing Polymer Structure as Hydrogel—Sample a A monomer solution comprising 300 g acrylic acid neutralized to 72 mol % with 50% sodium hydroxide solution, the quantity of water shown in Table 2 under "WS", 0.38 g polyethylene glycol-300-diacrylate and 1.14 g allyloxypolyethylene glycol acrylic acid ester was freed of dissolved oxygen by rinsing with nitrogen and cooled to the starting temperature of 4° C. After the addition of the starch compound shown in Table 2, mixing thoroughly and the attainment of the starting temperature, the initiator solution (0.3 g sodium peroxydisulfate in 10 g $H_2O$, 0.07 g 30% hydrogen peroxide solution in 1 g $H_2O$ and 0.015 g ascorbic acid in 2 g $H_2O$) was added. Following the attainment of the final temperature of approximately 100° C., the gel produced was ground to obtain granules with a particle size of approximately 1 to 3 mm, shown in Table 2a as samples α1 to α4. The water content of the non-dried hydrogen gels was 45 to 65%.

TABLE 2a

| Example | Starch compound | Quantity of starch compound [%] | WS - quantity of acrylic acid [% in monomer solution] | Sample |
|---|---|---|---|---|
| 1a | Type 1 | 5 | 30-441.65 g water | a1 |
| 1b | Type 1 | 5 | 27.5-486.69 g water | a2 |
| 1c | Type 1 | 5 | 25-531.82 g water | a2 |
| 1d (reference) | None | 0 | 30-441.65 g water | a4 |

Examples 1e-1 to 1e-24

Incorporation of Starch Compounds in Hydrogel—Sample a of Samples V2

The hydrogel obtained in example 1 without a starch compound was mixed with the quantity of starch compound shown in Table 2b before further grinding and dried in accordance with the specifications in examples 2a and 3a, screened and post-crosslinked.

TABLE 2b

| | Starch type | | | |
|---|---|---|---|---|
| Quantity | 1 Samples | 2 Samples | 3 Samples | 4 Samples |
| 5% | V2-1a | V2-2a | V2-3a | V2-4a |
| 10% | V2-1b | V2-2b | V2-3b | V2-4b |
| 20% | V2-1c | V2-2c | V2-3c | V2-4c |

Example 2

Production of a Non-Post-Crosslinked Water-Absorbing Polymer Structure as a Powder—Sample b Samples a1 to a4 were dried for 120 minutes at 150° C. The dried polymer was coarsely crushed, ground and screened to a powder with a particle size of 150 to 850 μm and samples b1 to b4 with a mean particle size according to ERT 420.2-20 of 520 to 540 μm obtained. The water content determined according to ERT 430.1-99 was 5% for all samples b1 to b4. Further properties are shown in Table 3a.

TABLE 3a

| | Example | | | |
|---|---|---|---|---|
| Sample | 2a b1 | 2b b2 | 2c b3 | 2d (reference) b4 |
| CRC [g/g] | 32.1 | 32.5 | 34.6 | 35.1 |

Examples 2e-1 to 2e-24

Incorporation of Starch Compounds on Powdery Non-Post-Crosslinked Water-Absorbing Polymer Structures—Sample a of Samples V4

The sample b4 obtained in example 2 was blended in a roller mixer of the type BTR 10 made by the company Fröbel GmbH Germany with the quantities of starch compound shown in Table 3b and post-crosslinked according to the specification for example 3a.

TABLE 3b

| | Starch type | | | |
|---|---|---|---|---|
| Quantity | 1 Samples | 2 Samples | 3 Samples | 4 Samples |
| 5% | V4-1a | V4-2a | V4-3a | V4-4a |
| 10% | V4-1b | V4-2b | V4-3b | V4-4b |
| 20% | V4-1c | V4-2c | V4-3c | V4-4c |

Example 3a

Production of a Post-Crosslinked Water-Absorbing Polymer Structure as a Powder—Sample c For post-crosslinking, 100 g of the powders of samples b1 to b4 obtained above were mixed with vigorous agitation with a solution of 1 g 1,3-dioxalan-2-one, 3 g water and then heated for 30 minutes in an oven brought to 180° C. The samples c1 to c4 obtained in this way had a mean particle size according to ERT 420.2-02 of 525 to 573 μm. The water content in sample c according to ERT 430.1-99 was 4.5%. Details may be found in Table 4a.

TABLE 4a

| | Example | | | |
|---|---|---|---|---|
| Sample | 2a c1 | 3b c2 | 3c c3 | 3d (reference) c4 |
| AAP0.7 [g/g] | 23.6 | 24.4 | 25.3 | 25.0 |
| CRC [g/g] | 27.2 | 27.3 | 29.2 | 30.6 |
| SFC [×$10^{-7}$ $cm^3$ sec/g] | | | 29.2 | 20.0 |

Examples 3e-1 to 3e-24

Incorporation of Starch Compounds on Powdery Post-Crosslinked Water-Absorbing Polymer Structure—Sample a of Samples V6

The sample c4 obtained in example 3a was blended in a roller mixer of the type BTR 10 made by the company Fröbel GmbH Germany with the quantities of starch compound shown in Table 4b.

TABLE 4b

| | Starch type | | | |
|---|---|---|---|---|
| Quantity | 1 Samples | 2 Samples | 3 Samples | 4 Samples |
| 5% | V6-1a | V6-2a | V6-3a | V6-4a |
| 10% | V6-1b | V6-2b | V6-3b | V6-4b |
| 20% | V6-1c | V6-2c | V6-3c | V6-4c |

Examples 3e-25 to 3e-48

Incorporation of Starch Compounds on Powdery Post-Crosslinked Water-Absorbing Polymer Structure Containing Starch Compounds—Sample a of Samples V1V6

The sample c3 obtained in example 3a was blended in a roller mixer of the type BTR 10 made by the company Fröbel GmbH Germany with the quantities of starch compound shown in Table 4c.

TABLE 4c

| | Starch type | | | |
|---|---|---|---|---|
| Quantity | 1 Samples | 2 Samples | 3 Samples | 4 Samples |
| 5% | V1V6-1a | V1V6-2a | V1V6-3a | V1V6-4a |
| 10% | V1V6-1b | V1V6-2b | V1V6-3b | V1V6-4b |
| 20% | V1V6-1c | V1V6-2c | V1V6-3c | V1V6-4c |

Examples 4.1 for samples V2V6

Incorporation of Starch Compounds on Powdery Post-Crosslinked Water-Absorbing Polymer Structure Containing Starch Compounds—Sample a of Samples V2V6

The samples V2-1a to V2-4-c were blended in a roller mixer of the type BTR 10 made by the company Fröbel GmbH Germany with the starch compound of types 1 to 4 in each case in starch compound quantities of 5%, 10% and 20%.

Examples 4.2 for samples V4V6

Incorporation of Starch Compounds on Powdery Post-Crosslinked Water-Absorbing Polymer Structure—Sample a of Samples V4V6

Samples V4-1a to V4-4-c were blended in a roller mixer of the type BTR 10 made by the company Fröbel GmbH Germany with the starch compound of types 1 to 4 in each case in starch compound quantities of 5%, 10% and 20%.

Example 4

Polymerization

A monomer solution comprising 280 g of the above obtained acrylic acid neutralized to 70 mol % with sodium hydroxide solution, 466.8 g water, 1.4 g polyethylene glycol-300-diacrylate and 1.68 g allyloxypolyethylene glycol acrylic acid ester was freed of dissolved oxygen by rinsing with nitrogen and cooled to the starting temperature of 4° C. After the attainment of the starting temperature, the initiator solution (0.1 g 2,2'-azobis-2-amidinpropane-dihydrochloride in 10 g $H_2O$, 0.3 g sodium peroxydisulfate in 10 g $H_2O$, 0.07 g 30% hydrogen peroxide solution in 1 g $H_2O$ and 0.015 g ascorbic acid in 2 g $H_2O$) was added. Following the attainment of the final temperature of approximately 100° C., the gel produced was comminuted and dried at 150° C. for 90 minutes. The dried polymer was coarsely crushed, ground and screened to produce a powder A with a particle size of 150 to 850 μm.

For the post-crosslinking, 100 g of the powder A obtained above was mixed under vigorous agitation with a solution of 1 g 1.3 dioxalan-2-one, 3 g water and 0.5 g aluminum sulfate-18-hydrate and then heated for 40 minutes in an oven that had been brought to 180° C. The powder B obtained in this way had a mean particle size according to ERT 420.2-02 of 530 μm. The water content determined in powder A according to ERT 430.1-99 was 4.5%.

The powder B was mixed with a starch compound of type 3 in a polymer:starch weight ratio of 4:1 under dry conditions and then further homogenized for 45 minutes in a roller mixer of the type BTR 10 made by the company Fröbel GmbH Germany. Powder C had a biodegradability according to the modified Sturm test after 28 days of 39% and a CRC value of 29.9 g/g.

Core Production

The cores were formed by means of a mixture of in each case 48.6% by weight of the above-described superabsorbent compositions V6-2b or V6-2c based on the core and 48.6% by weight of cellulose fibers Stora Fluff EF semitreated from the company Stora-Enzo AB Sweden and 2.8% by weight of a two-component fiber comprising 50% by weight each of polypropylene (PP) or polyethylene (PE) with a PP core and PE sheath made by the company Fibervision A/S Denmark using an air laid method with an M&J machine (width 40 cm, effective width 36 cm, operational settings: belt speed 3 m/min, fluff feed on hammer mill 3.1 m/min, polymer feed 380 g/min, two-component fiber in 10 g portions discharged approximately once/min), whereby the absorbent polymer was input homogeneously. Cores with a basic weight of 756 g/m$^2$ and a density of 0.2 g/cm$^3$ were used for the tests. The cores had a length of 300 mm and a width of 120 mm. The results of the core analysis for the liquid additions described as "insults" in each case are shown in Tables 5a and 5b.

TABLE 5a

| Acquisition time as 6 times determination | | | |
|---|---|---|---|
| Sample | 1st insult | 2nd insult | 3rd insult |
| V6-2b | 22 s | 200 s | 562 s |
| V6-2c | 20 s | 167 a | 468 s |
| 3d (reference) | 23 s | 290 s | 797 s |

TABLE 5b

| Liquid distribution as 6 times determination | | | |
|---|---|---|---|
| Sample | 1st insult | 2nd insult | 3rd insult |
| V6-2b | 10 cm | 15 cm | 19.8 cm |
| V6-2c | 10 cm | 16 cm | 20.3 cm |
| 3d (reference) | 10 cm | 14 cm | 18.2 cm |

The superabsorbent compositions according to the invention have a better acquisition time and liquid distributions compared to a reference sample which does not contain a starch compound.

The invention claimed is:

1. A method for the production of a superabsorbent composition comprising the process steps:
   i. producing a hydrogel by radical polymerization of an aqueous monomer solution containing an ethylenically unsaturated acid-group-containing monomer including acrylic acid and methacrylic acid and a crosslinking agent, wherein the monomer solution has a monomer content in the range from 20 to 30%;

ii. drying the hydrogel to obtain a water-absorbing polymer structure;
iii. surface post-crosslinking of the water-absorbing polymer structure with a post-crosslinking agent to obtain a surface-crosslinked water-absorbing polymer structure;
iv. incorporating from about 5 wt % to 20 wt % of a water-soluble powder starch compound based on the weight of the superabsorbent composition wherein the powder starch compound is water-soluble if at least about 30 g of powder starch compound may be dissolved in a liter of deionized water at a temperature of 20° C., in at least two of the following variants
  V2. after process step i. and prior to process step ii. into the hydrogel
  V3. in process step ii
  V5. in process step iii
  wherein the starch compound comprises less than about 20% amylose and is more than about 75% carboxymethylated, and wherein the starch compound has a weight average particle size from 20 to 80 µm, and less than 10 wt % of the particles having a particle size of less than about 5 µm and less than 10 wt % of the particles having a particle size of more than about 90 µm wherein the superabsorbent composition has the following properties:
    Z1 a retention (CRC) of from about 25 g/g to 35.1 g/g,
    Z2 an absorption at pressure ($AAP_{0.7}$) of from about 15 g/g to 25.3 g/g,
    Z3 a permeability (SFC) of from about $20 \times 10^{-7}$ cm$^3$ sec/g to $29.2 \times 10^{-7}$ cm$^3$ sec/g, and
    Z4 a biodegradability determined according to the method described herein after 28 days of from about 25% to 39%.

2. The method according to claim 1, wherein the starch compound has at least one of the following properties:
  S1 a free absorption (FA) of at least about 9 g/g,
  S2 a retention (CRC) of at least about 7 g/g,
  S3 an absorption at pressure ($AAP_{0.3}$) of at least about 2 g/g,
  S4 an absorption at pressure ($AAP_{0.7}$) of at least about 2 g/g, and
  S5 a pH value in the range from about 9 to about 14.

3. The method according to claim 1, wherein at least one first starch compound SI is incorporated in the variant V2.

4. The method according to claim 1, wherein the starch compound is used in a quantity of a maximum of about 30% by weight based on the monomer used.

5. The method according to claim 1, wherein the monomer solution has a monomer content in the range from 22.5 to 27.5% by weight based on the monomer solution.

6. The method according to claim 1, wherein the starch compound has a solution viscosity according to the method specified herein in the range of from about 20,000 to about 50,000 mPas.

7. The method according to claim 1, wherein the starch compound comprises less than about 10% by weight of cyclic or branched polysaccharides.

8. A method for the production of a superabsorbent composition comprising the process steps:
  i. producing a hydrogel by radical polymerization of an aqueous monomer solution containing an ethylenically unsaturated acid-group-containing monomer including acrylic acid and methacrylic acid and a crosslinking agent, wherein the monomer solution has a monomer content in the range from 20 to 30%;
  ii. drying the hydrogel to obtain a water-absorbing polymer structure;
  iii. surface post-crosslinking of the water-absorbing polymer structure with a post-crosslinking agent to obtain a surface-crosslinked water-absorbing polymer structure;
  iv. incorporating from about 5 wt % to 20 wt % of a water-soluble powder starch compound based on the weight of the superabsorbent composition wherein the powder starch compound is water-soluble if at least about 30 g of powder starch compound may be dissolved in a liter of deionized water at a temperature of 20° C., in at least two of the following variants
    V3. in process step ii
    V4. after process step ii. and prior to process step iii. into the water-absorbing polymer structure
    V5. in process step iii,
    wherein the starch compound comprises less than about 20% amylose and is more than about 75% carboxymethylated, and wherein the starch compound has a weight average particle size from 20 to 80 µm, and less than 10 wt % of the particles having a particle size of less than about 5 µm and less than 10 wt % of the particles having a particle size of more than about 90 µm wherein the superabsorbent composition has the following properties:
      Z1 a retention (CRC) of from about 25 g/g to 35.1 g/g,
      Z2 an absorption at pressure ($AAP_{0.7}$) of from about 15 g/g to 25.3 g/g,
      Z3 a permeability (SFC) of from about $20 \times 10^{-7}$ cm$^3$ sec/g to $29.2 \times 10^{-7}$ cm$^3$ sec/g, and
      Z4 a biodegradability determined according to the method described herein after 28 days of from about 25% to 39%.

9. The method according to claim 8, wherein the starch compound has at least one of the following properties:
  S1 a free absorption (FA) of at least about 9 g/g,
  S2 a retention (CRC) of at least about 7 g/g,
  S3 an absorption at pressure ($AAP_{0.3}$) of at least about 2 g/g,
  S4 an absorption at pressure ($AAP_{0.7}$) of at least about 2 g/g, and
  S5 a pH value in the range from about 9 to about 14.

10. The method according to claim 8, wherein the starch compound is used in a quantity of a maximum of about 30% by weight based on the monomer used.

11. The method according to claim 8, wherein the monomer solution has a monomer content in the range from 22.5 to 27.5% by weight based on the monomer solution.

12. The method according to claim 8, wherein the starch compound has a solution viscosity according to the method specified herein in the range of from about 20,000 to about 50,000 mPas.

13. The method according to claim 1, wherein the starch compound comprises less than about 10% by weight of cyclic or branched polysaccharides.

14. A method for the production of a superabsorbent composition comprising the process steps:
  i. producing a hydrogel by radical polymerization of an aqueous monomer solution containing an ethylenically unsaturated acid-group-containing monomer including acrylic acid and methacrylic acid and a crosslinking agent, wherein the monomer solution has a monomer content in the range from 20 to 30%;
  ii. drying the hydrogel to obtain a water-absorbing polymer structure;
  iii. surface post-crosslinking of the water-absorbing polymer structure with a post-crosslinking agent to obtain a surface-crosslinked water-absorbing polymer structure;

iv. incorporating from about 5 wt % to 20 wt % of a water-soluble powder starch compound based on the weight of the superabsorbent composition wherein the powder starch compound is water-soluble if at least about 30 g of powder starch compound may be dissolved in a liter of deionized water at a temperature of 20° C., in at least two of the following variants
V3. in process step ii,
V5. in process step iii,
V6. after process step iii onto the surface-crosslinked water-absorbing polymer structure,
wherein the starch compound comprises less than about 20% amylose and is more than about 75% carboxymethylated, and wherein the starch compound has a weight average particle size from 20 to 80 μm, and less than 10 wt % of the particles having a particle size of less than about 5 μm and less than 10 wt % of the particles having a particle size of more than about 90 μm wherein the superabsorbent composition has the following properties:
Z1 a retention (CRC) of from about 25 g/g to 35.1 g/g,
Z2 an absorption at pressure ($AAP_{0.7}$) of from about 15 g/g to 25.3 g/g,
Z3 a permeability (SFC) of from about $20 \times 10^{-7}$ cm$^3$ sec/g to $29.2 \times 10^{-7}$ cm$^3$ sec/g, and
Z4 a biodegradability determined according to the method described herein after 28 days of from about 25% to 39%.

15. The method according to claim 14, wherein the starch compound has at least one of the following properties:
S1 a free absorption (FA) of at least about 9 g/g,
S2 a retention (CRC) of at least about 7 g/g,
S3 an absorption at pressure ($AAP_{0.3}$) of at least about 2 g/g,
S4 an absorption at pressure ($AAP_{0.7}$) of at least about 2 g/g, and
S5 a pH value in the range from about 9 to about 14.

16. The method according to claim 15, wherein the starch compound is used in a quantity of a maximum of about 30% by weight based on the monomer used.

17. The method according to claim 15, wherein the monomer solution has a monomer content in the range from 22.5 to 27.5% by weight based on the monomer solution.

18. The method according to claim 15, wherein the starch compound has a solution viscosity according to the method specified herein in the range of from about 20,000 to about 50,000 mPas.

19. The method according to claim 15, wherein the starch compound comprises less than about 10% by weight of cyclic or branched polysaccharides.

* * * * *